United States Patent [19]
Goto et al.
[11] 4,415,641
[45] Nov. 15, 1983

[54] ELECTROPHOTOGRAPHIC LIGHT-SENSITIVE ELEMENT

[75] Inventors: Satoshi Goto; Akira Kinoshita, both of Hino; Yoshiaki Takei; Yoshihide Fujimaki, both of Hachioji, all of Japan

[73] Assignee: Konishiroku Photo Industry Co., Ltd., Tokyo, Japan

[21] Appl. No.: 353,934

[22] Filed: Mar. 2, 1982

[30] Foreign Application Priority Data

Mar. 11, 1981 [JP] Japan ........ 56-35069

[51] Int. Cl.[3] ........ G03C 1/16; C07D 209/82

[52] U.S. Cl. ........ 430/59; 430/58; 430/79; 430/77

[58] Field of Search ........ 430/76, 79, 74, 77, 430/58, 59

[56] References Cited

U.S. PATENT DOCUMENTS

| | | | |
|---|---|---|---|
| 3,189,447 | 6/1965 | Neugebauer et al. | 430/77 |
| 3,287,119 | 11/1966 | Hoegl | 430/79 |
| 3,697,264 | 10/1972 | Podhajny | 430/79 |
| 3,820,989 | 6/1974 | Rule et al. | 430/74 |
| 3,895,945 | 7/1975 | Watarai et al. | 430/79 |
| 4,006,017 | 2/1977 | Williams et al. | 430/79 |
| 4,091,208 | 5/1978 | Okazaki et al. | 430/79 |
| 4,251,614 | 2/1981 | Sasaki et al. | 430/79 |

FOREIGN PATENT DOCUMENTS

| | | | |
|---|---|---|---|
| 52-34735 | 3/1977 | Japan | 430/79 |
| 52-35642 | 3/1977 | Japan | 430/79 |

*Primary Examiner*—Edward C. Kimlin
*Assistant Examiner*—Merrell C. Cashion, Jr.
*Attorney, Agent, or Firm*—Frishauf, Holtz, Goodman & Woodward

[57] ABSTRACT

An electrophotographic light-sensitive element comprising a conductive support which supports a light-sensitive layer containing a carbazole derivative of the formula:

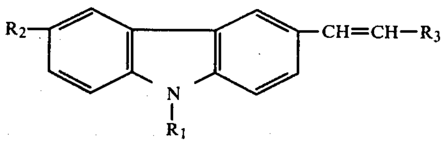

wherein $R_1$ is an aryl group, $R_2$ is hydrogen, a halogen, an alkyl, an alkoxy, an amino or hydroxy group, and $R_3$ is an aryl, or a heterocyclic group.

14 Claims, 6 Drawing Figures

ELECTROPHOTOGRAPHIC LIGHT-SENSITIVE ELEMENT

The present invention relates to an electrophotographic light-sensitive element, and more particularly to a novel electrophotographic light-sensitive element having a light-sensitive layer containing as the principal component thereof an organic photoconductive compound.

As electrophotographic light-sensitive elements there have been widely known those which have a light-sensitive layer containing as the principal component thereof an inorganic photoconductive material such as selenium zinc oxide, cadmium sulfide or the like. However, these are not necessarily satisfactory in characteristics such as stability against heat, durability, and the like, and have problems in the manufacture and handling thereof due to their toxicity.

On the other hand, an electrophotographic light-sensitive element having a light-sensitive layer containing as the principal component thereof an organic photoconductive compound has many advantages such as being relatively readily manufactured, being easily handled, and being excellent generally in stability against heat as compared with a selenium light-sensitive element and the like. As such organic photoconductive compounds, poly-N-vinyl carbazole is well known, and an electrophotographic light-sensitive element having a light-sensitive layer containing as the principal component thereof a charge-transfer complex formed from said poly-N-vinyl carbazole and a Lewis acid such as 2,4,7-trinitro-9-fluorenone is a practical reality. While on the other hand, an electrophotographic light-sensitive element is known which has a multilayer type or dispersion type function-separative light-sensitive layer designed so that the carrier-generation function and carrier-transport function thereof are separately carried out by different materials; for example, an electrophotographic light-sensitive element having a light-sensitive layer comprising a carrier-generation layer composed of an amorphous selenium thin layer and a carrier-transport layer containing poly-N-vinyl carbazole in combination has been made a practical reality.

However, poly-N-vinyl carbazole, which is lacking in flexibility, has the disadvantages that a layer thereof is rather hard and brittle, tending to cause cracks and peeling, and therefore an electrophotographic light-sensitive element made of this material is inferior in the durability. In an attempt to overcome this disadvantage, a plasticizer is added to the material, the residual potential in the electrophotographic light-sensitive element prepared by the use of such material when applied to the electrophotographic process becomes larger, the residual potential being accumulated as the element is repeatedly used, thus gradually causing fog in the copied image.

Low molecular weight organic photoconductive compounds, on the other hand, since they generally have no film-forming ability, have to be used together with an appropriate binder, so that while it is advantageous that an appropriate selection of kind and composition ratio of the binder to be used permits one to control the physical properties or the electrophotographic characteristics of the layer to some extent. However, the kinds of organic photoconductive compounds having high compatibility with such binders are limited, and those which are applicable to the formation of the light-sensitive layer are few.

For example, 2,5-bis(p-diethylaminophenyl)-1,3,4-oxadiazole described in U.S. Pat. No. 3,189,447 has the disadvantage that when the compound, because of having low compatibility with a binder which is normally favorably usable as a material for a light-sensitive layer, is mixed with a binder such as, polyester, polycarbonate, in a required proportion to obtain a desirable electrophotographic characteristics deposit of crystals of the oxadiazole is often observed in the layer at a temperature above 50° C., thus deteriorating the electrophotographic characteristics in, such as, the charge retention and sensitivity.

In contrast to this, the diaryl alkane derivative described in U.S. Pat. No. 3,820,989, although no problem resides in the compatibility thereof with normal binders, has the disadvantage that the compound is poor in stability against light, so that when the compound is employed in a light-sensitive layer of an electrophotographic light-sensitive element which is subject to repetitive use, i.e. which is to be repeatedly charged and exposed, the sensitivity of said light-sensitive layer gradually deteriorates.

On the other hand, α-(9-anthryl)-β-[3-(N-ethyl-carbazolyl)]ethylene which has better compatibility with binders and can provide an electrophotographic light-sensitive element having relatively favorable initial characteristics, has the disadvantage that when the light-sensitive element is repeatedly used the sensitivity thereof gradually deteriorates with the accumulation of residual potential, so that the light-sensitive element containing said compound is insufficient in durability.

Thus, the present situation is that few organic photoconductive compounds having desirable characteristics practically usable in the manufacture of electrophotographic light-sensitive elements have been found to date.

It is an object of the present invention to provide an electrophotographic light-sensitive element containing a carrier-transport material consisting of an organic photoconductive compound which is excellent in compatibility with binders and stable against heat and light as well as excellent in carrier-transportability.

It is another object of the present invention to provide an electrophotographic light-sensitive element with a photo-conductive layer having excellent film strength and excellent stability during repetitive use.

It is a further object of the present invention to provide an electrophotographic light-sensitive element having high sensitivity and less residual potential.

It is still another object of the present invention to provide an electrophotographic light-sensitive body which, when used as a repetitive transfer type electrophotographic light-sensitive element which is subject to a number of repeated cycles of charging, exposure, development and transfer processes, is less liable to deteriorate by fatigue even after repeated use and is capable of preserving excellent durability and retaining stable characteristics over an extensive period of time.

We have found that these objects can be attained by using a specific carbazole derivative as a photoconductive material, and thus we have completed the present invention.

The foregoing objects can be attained by an electrophotographic light-sensitive element comprising on a photoconductive support a light-sensitive layer containing as the principal component a carbazole derivative having the formula:

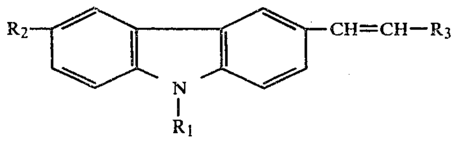

wherein $R_1$ represents aryl group, $R_2$ represents hydrogen, a halogen, an alkyl, alkoxy, amino, or hydroxy group, and $R_3$ represents an aryl, or a heterocyclic group.

Hereinabove, each of aryl, alkyl, alkoxy, amino and heterocyclic groups of $R_1$, $R_2$ and $R_3$ may be substituted.

According to one of the preferable embodiments of the invention, in the above formula (I), $R_1$ is selected from the group consisting of a phenyl group and a naphthyl group each of which group may be substituted by an alkyl group, preferably by one having 1 to 4 carbon atoms, an alkoxy group, preferably by one having 1 to 4 carbon atoms, a dialkylamino group preferably dimethylamino or diethylamino group, or chlorine atom or bromine atom; $R_2$ is selected from a group consisting of hydrogen atom, chlorine atom or bromine atom, or an alkyl group having 1 to 8, and more preferably 1 to 4 carbon atoms, an alkoxy group having 1 to 4 carbon atoms, a dialkylamino group preferably dimethylamino or diethylamino group or hydroxy group and $R_3$ is selected from a group consisting of a phenyl group, a naphthyl group, an anthryl group, a furyl group, a thienyl group, a carbazyl group, a benzfuryl and a benzthienyl group, each which group may be substituted by an alkyl group having 1 to 8, and more preferably 1 to 4 carbon atoms, an alkoxy group having 1 to 4 carbon atoms, a phenyl group which may be substituted with a dialkylamino group (preferably dimethylamino or diethylamino group), a diarylamino group (preferably diphenylamino group), a hydroxy group or a halogen atom.

In the present invention, an electrophotographic light-sensitive element which is excellent in electrophotographic characteristics such as the physical characteristics of the coated layer, charge retention, sensitivity, residual potential, and the like, and which not only is less deteriorated by fatigue even after being repeatedly used but stably retains said characteristics against heat and light, and thus is capable of displaying the very stable characteristics, may be prepared by using a carbazole derivative having the above Formula (I) as the photoconductive material of an electrophotographic light-sensitive element and by using the carbazole derivative of the present invention as the carrier-transport material of the so-called function-separative-type electrophotographic light-sensitive body which utilizes nothing but the carrier transportability of said carbazole derivative, and which carries out the carrier generation and carrier transport separately by different materials, respectively.

Examples of carbazole derivatives useful for the present invention covered by the foregoing Formula (I) are given hereinbelow, but, of course the carbazole derivatives of the present invention are not limited thereto.

Exemplified Compounds (1)

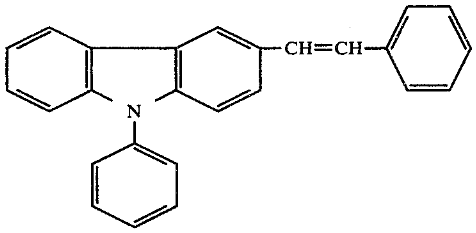

(2)

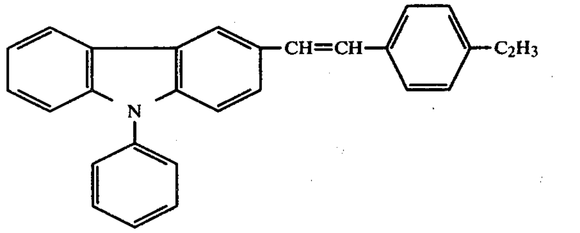

(3)

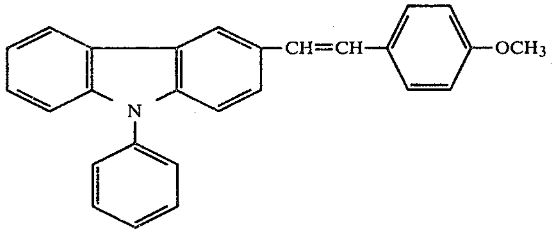

(4)

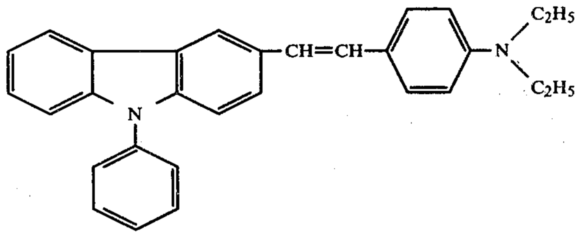

(5)

-continued
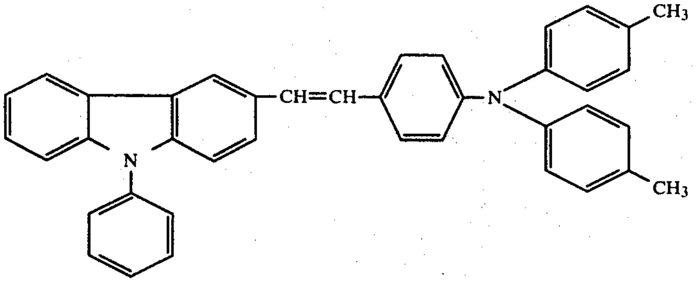
(6)
(7)
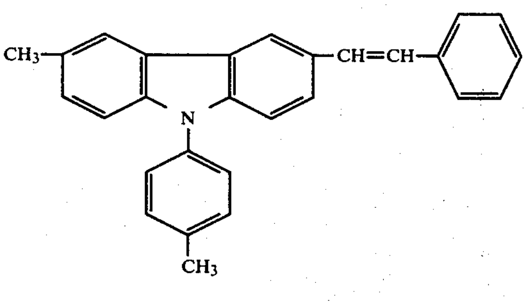
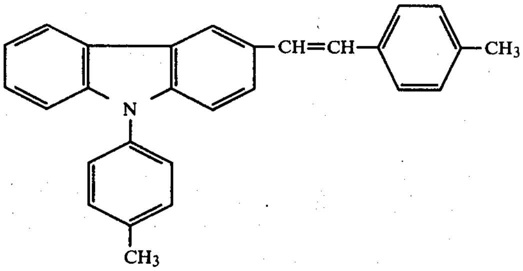
(8)
(9)
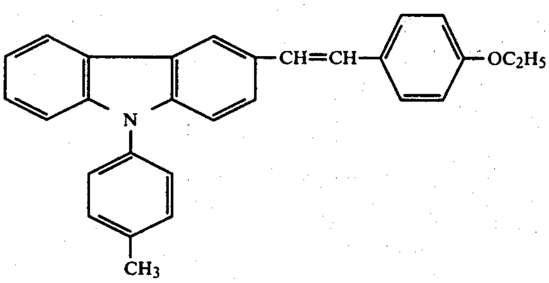
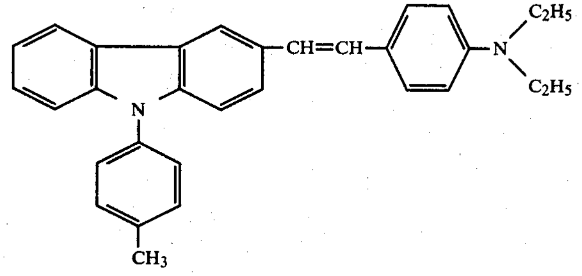
(10)
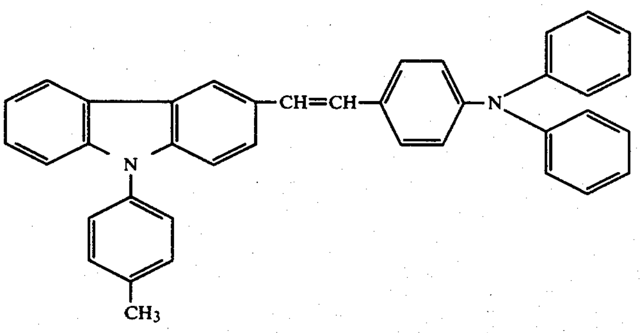
(11)
(12)
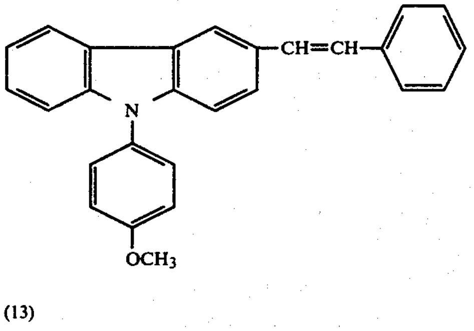
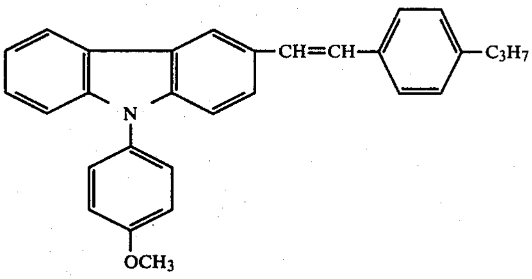
(13)
(14)

-continued
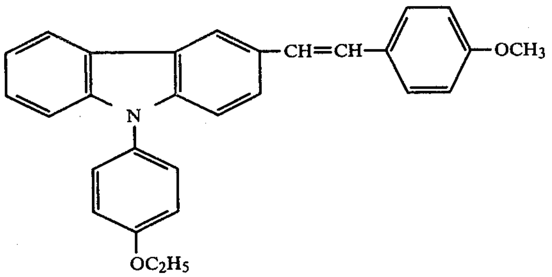
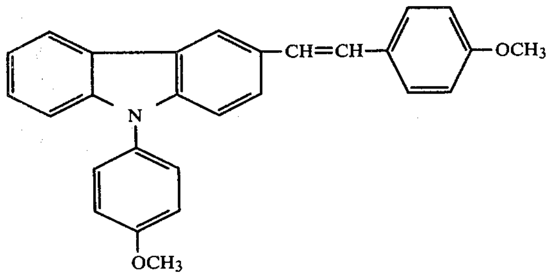
(15)
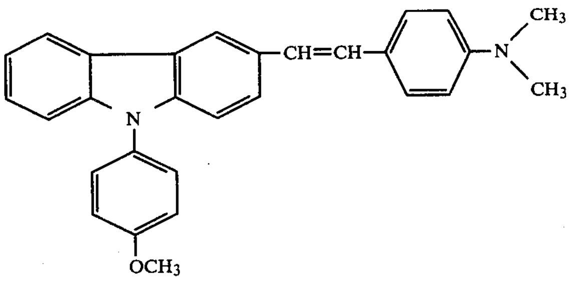
(16)
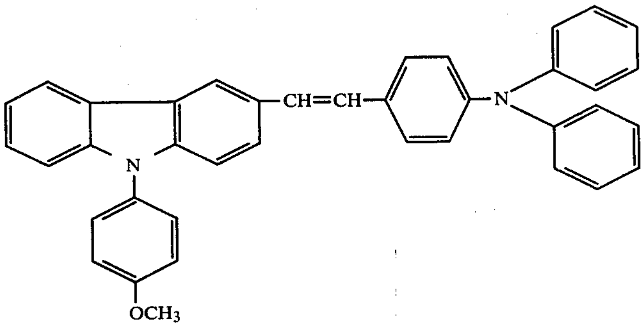
(17) (18)
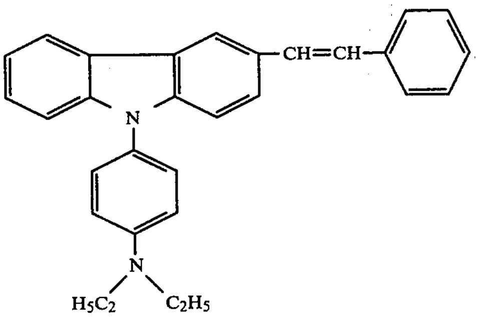
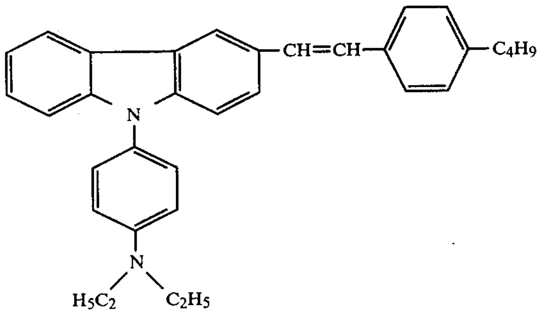
(19) (20)
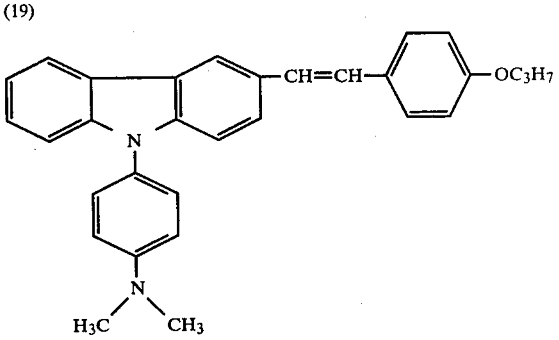
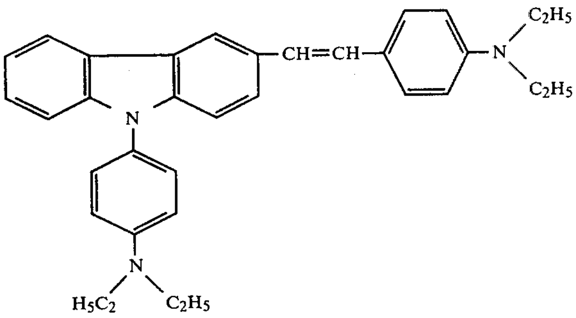
(21) (22)

-continued
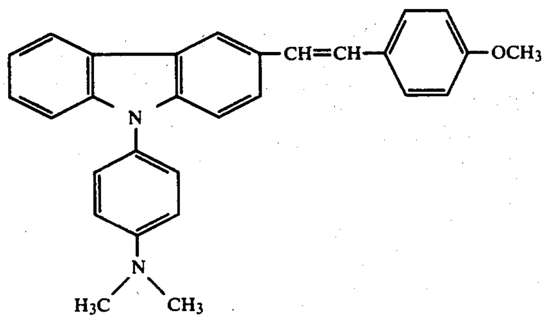
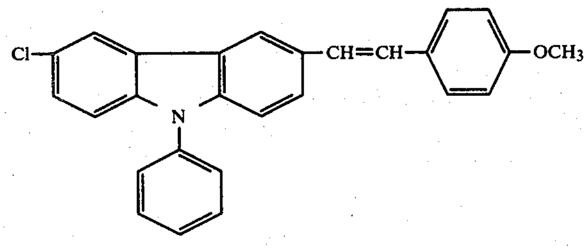
(23)
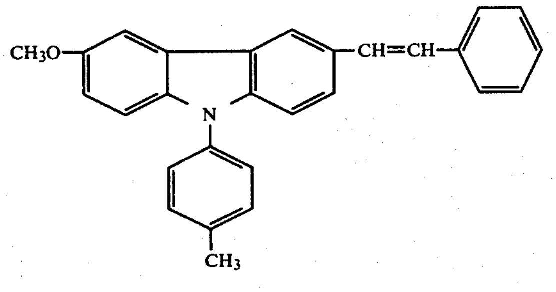
(24)
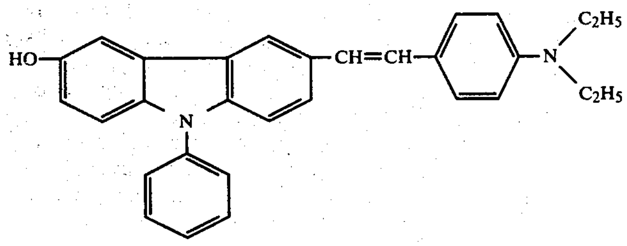
(25)
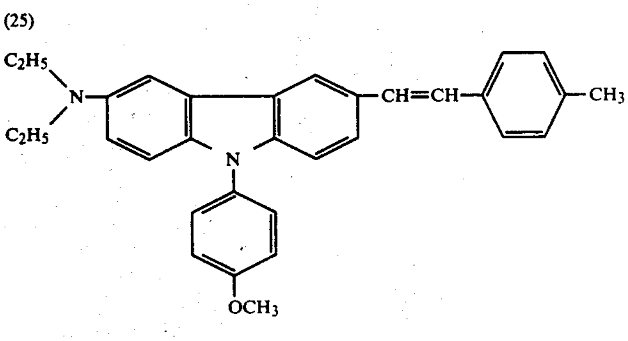
(26)
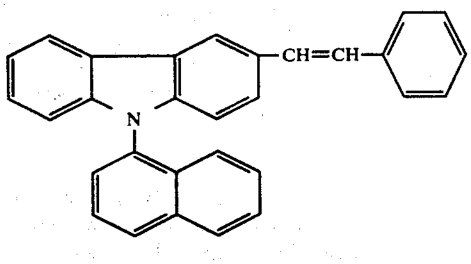
(27)
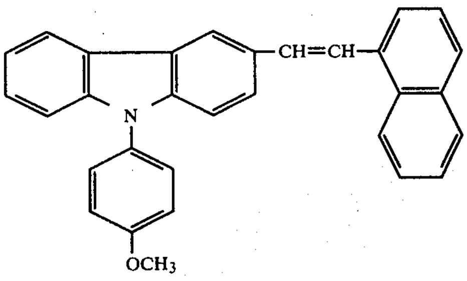
(28)
(29)

-continued

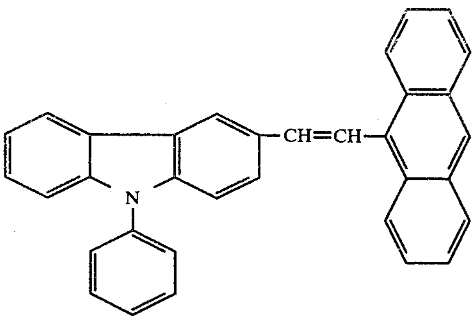

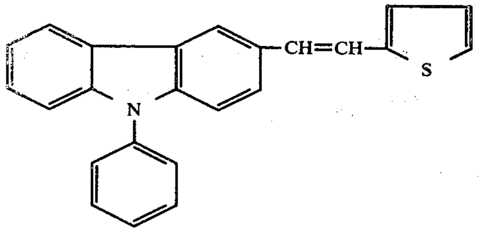

(30)

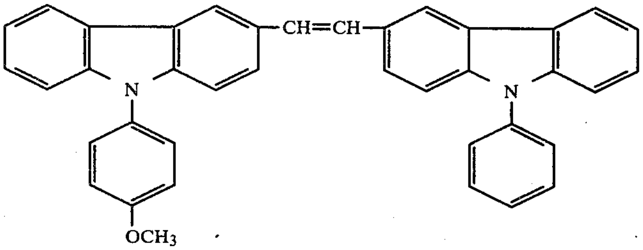

These carbazole derivatives may be readily synthesized by known methods; for example, by the condensation reaction of N-substituted carbazole-3-carbaldehyde having the formula (III) with phosphonic acid diester having the formula (IV) in a solvent such as N,N-dimethyl formamide in the presence of a strong base.

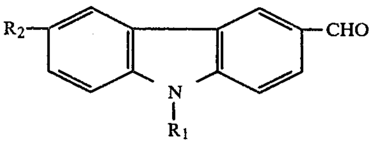

+

Formula [III]

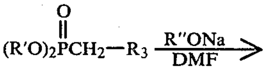

Formula [IV]

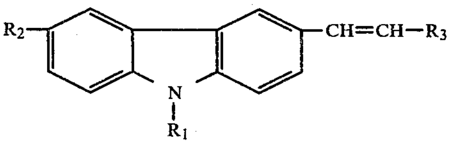

Formula [I]

wherein $R_1$, $R_2$ and $R_3$ respectively represent the same atoms or groups as defined in Formula (I), and R' and R'' independently represent an alkyl group such as methyl, ethyl, etc.

Typical synthesis methods of carbazole derivatives to be used in the present invention are illustrated in detail below:

SYNTHESIS EXAMPLE 1

Synthesis of Exemplified Compound (11)

22.8 g (0.1 mol) of diethyl-benzyl phosphonate were dissolved into 100 ml of N,N-dimethyl formamide, and to the solution, with cooling by ice, were little by little added 10.8 g (0.2 mol) of sodium methoxide. To the mixture was subsequently added dropwise spending 20 minutes a solution of 30.1 g (0.1 mol) of N-(p-methoxyphenyl)carbazole-3-carbaldehyde dissolved into 200 ml of N,N-dimethyl formamide. The resulting mixture was stirred in the ice-cooled condition for one hour and then further stirred for four hours at room temperature. After that, 300 ml of iced water were added to the mixture to deposit a precipitate, which was then filtered and recrystallized twice from acetonitrile, thereby obtaining a colorless crystalline product.

Yield: 30.9 g, 82.5%

M.P.: 136°-137° C.

SYNTHESIS EXAMPLE 2

Synthesis of Exemplified Compound (7)

24.2 g (0.1 mol) of diethyl α-xylene phosphonate were dissolved into 100 ml of N,N-dimethyl formamide, and to the solution, with cooling by ice, were little by little added 10.8 g (0.2 mol) of sodium methoxide. To the mixture was then added dropwise spending 15 minutes a solution of 30.1 g (0.1 mol) of N-(p-tolyl)carbazole-3-carbaldehyde dissolved into 200 ml of N,N-dimethyl formamide. The resulting mixture was stirred for one hour in the ice-cooled condition, and then further stirred for two hours at room temperature, to which were then added 200 ml of iced water to deposit a precipitate. The precipitate was filtered and recrystallized with the use of a mixed solvent of ethanol with benzene in the ratio of 5 to 1, and then further recrystallized from acetonitrile, thus obtaining a colorless crystalline product.

Yield: 28.4 g, 72.9%

M.P.: 122°-123° C.

The carbazole derivatives of the present invention, because of having little or no sensitivity in visible region, need to be subjected to a sensitizing treatment in order to be exposed to visible rays. For sensitizing organic photoconductive compounds there have been suggested various methods. A first method is such that an organic dye is added to the compound to provide a spectral sensitivity therefor. A second method is such that a charge-transfer complex is formed to sensitize the compound. The carbazole derivatives of the present invention, since they are electron-donating materials, are desirably used in combination with an electron-accepting material. A third method is to make use of the carrier transportability of the organic photoconductive compound and use in combination other carrier generation material such as organic dyes, pigments or inorganic photoconductive material in combination with the organic photoconductive compound, thereby providing a function-separative-type light-sensitive element.

Any one of the above sensitizing methods may optionally be applied to the carbazole derivatives of the present invention, and an appropriate method may be selected according to required characteristics of the element.

The following are typical examples of spectral sensitizing organic dyes applicable to the present invention:

(A-1) Triphenyl methane dyes such as methyl violet, crystal violet, malachite green, and the like.
(A-2) Xanthene dyes such as erythrocin, rose bengal, and the like.
(A-3) Thiazine dyes such as methylene blue, methylene green, and the like.
(A-4) Oxazine dyes such as Capri blue, Meldola blue, and the like.
(A-5) Cyanine dyes such as thiocyanine, oxacyanine, and the like.
(A-6) Styryl dyes such as p-dimethylaminostyryl quinoline, and the like.
(A-7) Pyrylium salt dyes such as pyrylium salts, thiapyrylium salts, benzopyrylium salts, and the like.
(A-8) 3,3'-dicarbazolyl methane dyes.

These dyes may be used also as carrier-generation materials. In addition to the above dyes, those usable as carrier-generation materials are:

(B-1) Azo dyes such as monoazo dye, disazo dye, trisazo dye, and the like.
(B-2) Perylene dyes such as perylenic acid anhydride, perylenic acid imide, and the like.
(B-3) Indigoid dyes such as indigo, thioindigo, and the like.
(B-4) Polycyclic quinones such as anthraquinone, pyrenequinone, flavanthrones, and the like.
(B-5) Quinacrydone dyes.
(B-6) Bis-benzimidazole dyes.
(B-7) Indanthrone dyes.
(B-8) Squarylium dyes.
(B-9) Phthalocyanine dyes such as metal phthalocyanine, metal free phthalocyanine, and the like.
(B-10) Selenium and selenium alloy.
(B-11) Inorganic photoconductive materials such as CdS, CdSe, and the like.
(B-12) Co-crystalline complexes formed from pyrylium salt dyes, thiapyrylium salt dyes and polycarbonates.

As electron-accepting materials capable of forming charge-transfer complexes with carbazole derivatives of the present invention, there may be used such Lewis acids as 2,4,7-trinitrofluorenone, 2,4,5,7-tetranitrofluorenone, chloranyl, tetracyanoquinodimethane, and the like.

Meanwhile, chemical sensitizers may also be effectively used for the light-sensitive element of the present invention.

Carbazole derivatives used in the present invention have no film-forming-ability in themselves, so that they are used in combination with various binder materials to thereby form a light-sensitive layer.

As binder materials used herein, although any conventional ones may be used, hydrophobic, highly dielectric, insulating film-formable macromolecular polymers are desirable. Such macromolecular polymers include, e.g., the following compounds, but are not limited thereto:

(C-1) Polycarbonates.
(C-2) Polyesters.
(C-3) Methacrylic resins.
(C-4) Acrylic resins.
(C-5) Polyvinyl chloride.
(C-6) Polyvinylidene chloride.
(C-7) Polystyrenes.
(C-8) Polyvinyl acetate.
(C-9) Styrene-butadiene copolymers.
(C-10) Vinylidene chloride-acrylonitrile copolymers.
(C-11) Vinyl chloride-vinyl acetate copolymers.
(C-12) Vinyl chloride-vinyl acetate-maleic anhydride copolymers.
(C-13) Silicone resins.
(C-14) Silicone-alkyd resins.
(C-15) Phenol-formaldehyde resins.
(C-16) Styrene-alkyd resins.
(C-17) Poly-N-vinyl carbazole.

These binder materials may be used singly or in the form of a mixture of two or more kinds thereof.

The light-sensitive element of the present invention, as shown in FIG. 1 and FIG. 2, may comprise a conductive support 1 provided thereon with a light-sensitive layer 4 superposedly composed of a carrier-generation layer 2 containing as the principal component thereof a carrier-generation material and a carrier-transport layer 3 containing as the principal component thereof a carbazole derivative of the present invention. As shown in FIG. 3 and FIG. 4, this light-sensitive layer 4 may be provided through an interlayer 5 on conductive layer 1. When light-sensitive layer 4 is of a two-layer composition, a light-sensitive element having most excellent electrophotographic characteristics can be obtained. And in the present invention, as shown in FIG. 5 and FIG. 6, conductive support 1 may also be provided directly or through interlayer 5 thereon with a layer 6 consisting principally of said carrier-transport material into which a fine-grained carrier-generation material 7 is dispersed. Alternatively, without using the carrier-generation material, a sensitizing dye or Lewis acid or the like may be added to the carrier-transport material to provide a single-layered light-sensitive layer 4 in the same manner as shown in FIG. 5 and FIG. 6. In this manner satisfactory results can be obtained.

Where light-sensitive layer 4 is of a two-layer composition, which of carrier-generation layer 2 or carrier-transport layer 3 should be positioned as the upper layer is determined depending upon the selection of the charging polarity, whether positive or negative. When the light-sensitive layer is used with the negative charge, it is more advantageous that carrier-transport layer 3 be positioned as the upper layer because the carbazole derivative in the carrier-transport layer has a high transportability to the positive hole.

Carrier-generation layer 2 composing the two-layered light-sensitive layer 4 may be formed directly on conductive support 1 or carrier-transport layer 3 or, when necessary, provided on an interlayer such as an adhesive layer, barrier layer, etc., in any of the following means:

(1) vacuum deposition, (2) the means in which the carrier-generation material is dissolved into an appropriate solvent and the solution is then coated, and (3) the means in which the carrier-generation material is finely dispersed into a dispersion medium by means of a ball mill or a homomixer, and the dispersed liquid obtained, if necessary, after mixing with a binder, is coated. The thus formed carrier-generation layer 2 should have a thickness of preferably from 0.01 to 5 microns, more preferably from 0.05 to 3 microns.

The thickness of carrier-transport layer 3, although dependent on requirements, is preferably normally from 5 to 30 microns. The composition proportion of carrier-transport layer 3 is preferably 1 part by weight of the carrier-transport material consisting principally of the foregoing carbazole derivative to from 0.8 to 5 parts by weight of a binder material, but in the case of forming light-sensitive layer 4 into which a powdery carrier-generation material has been dispersed, the proportion range should be preferably 1 part by weight of the carrier-generation material to not more than 5 parts by weight of the binder material. Where carrier-generation layer 2 is constituted as a dispersion type by a binder material, the similar proportion range of 1 part by weight of the carrier-generation material to not more than 5 parts by weight of the binder should likewise be used.

In addition, for conductive support 1 of the electrophotographic light-sensitive body of the present invention, there may be used materials such as, e.g., a metallic plate, or conductivity-provided paper, plastic film and the like coated, deposited or laminated with a metallic thin layer such as of aluminum, palladium, gold or conductive compounds such as conductive polymers, indium oxide, and the like. For interlayer 5 which may be an adhesive layer, barrier layer and the like, in addition to those macromolecular polymers used as the foregoing binders, there may be used organic macromolecular materials such as gelatin, casein, starch, polyvinyl alcohol, vinyl acetate, ethyl cellulose, carboxymethyl cellulose, and the like or aluminum oxide.

The present invention is illustrated in further detail with reference to examples below, but the embodiments of the present invention are not limited thereto.

EXAMPLE 1

An aluminum foil-laminated conductive polyester film support was coated with a 0.5-micron-thick carrier-generation layer by vacuum deposition of selenium. On this was formed a carrier-transport layer by coating a solution prepared by dissolving 6 parts by weight of Exemplified Compound (1) and 10 parts by weight of a polycarbonate "Panlite L-1250" (manufactured by Teijin Chemical Industry Co., Ltd.) into 90 parts by weight of 1,2-dichloroethane, so that the thickness thereof after drying was 11 microns, whereby an electrophotographic light-sensitive element of the present invention was produced.

The resulting electrophotographic light-sensitive body was measured for electrophotographic characteristics by means of an electrostatic copying paper analyzer "Model SP-428" (manufactured by Kawaguchi Electric Works Co., Ltd.); the surface potential $V_A$ when the surface of the light-sensitive layer of said light-sensitive body was charged for 5 seconds by the charging voltage of −6.0 kv, the exposure (half-decay exposure) $E\frac{1}{2}$ (lux.sec) required to reduce by half the surface potential $V_A$ by exposing the surface of the light-sensitive body to a tungsten light so that the illumination on said surface is 35 lux, and the surface potential (residual potential) $V_R$ after exposing with the exposure of 30 lux.sec. were found, respectively.

The cycle of the measurements was repeated 100 times. The results are shown in Table 1.

TABLE 1

| | 1st | 100th |
|---|---|---|
| $V_A$ (V) | −835 | −870 |
| $E\frac{1}{2}$ (lux.sec) | 8.1 | 8.4 |
| $V_R$ (V) | 0 | −5 |

As apparent from the above table, the results obtained in the 100th measurements show that the characteristics are stable just as those in the first measurements are.

Control 1

A control light-sensitive element intended to be compared with that in Example 1 was prepared in the same manner as in Example 1 with the exception that as the carrier-transport material there was used a derivative of a carbazole having the formula:

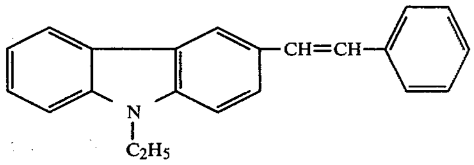

and the resulting light-sensitive body was subjected to measurements similar to those in Example 1. The results are shown in Table 2.

TABLE 2

| | 1st | 100th |
|---|---|---|
| $V_A$ (V) | −865 | −915 |
| $E\frac{1}{2}$ (lux.sec) | 10.2 | 14.1 |
| $V_R$ (V) | −10 | −75 |

As apparent from the above table, the control electrophotographic light-sensitive element is remarkably inferior to the electrophotographic light-sensitive element of the present invention.

Control 1-2

A control electrophotographic light-sensitive element was prepared in the same manner as in Example 1 with the exception that as the carrier-transport material there was used an N-phenyl carbazole having the formula:

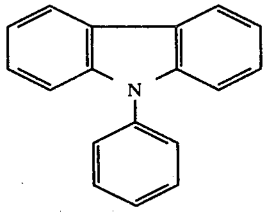

and the prepared light-sensitive body was subjected to measurements similar to those in Example 1, then the results showed $V_A=-675$ V, $E\frac{1}{2}=29.0$ lux.sec., and $V_R=-335$ V, and thus the light-sensitive body was remarkably inferior to the electrophotographic light-sensitive body of the present invention, so that the control light-sensitive body was unsuitable for practical use.

EXAMPLE 2

An aluminum foil-laminated conductive polyester film support was coated with a 0.05-micron-thick interlayer of a vinyl chloride—vinyl acetate—maleic anhydride copolymer "S-lec MF-10" (manufactured by Sekisui Chemical Co., Ltd.), and on this was formed a 0.5-micron-thick carrier-generation layer by the vacuum deposition of dibromoanthanthrone "Monolite Red 2Y" (C.I. No. 59300, manufactured by ICI), and further on this was formed a carrier-transport layer by coating a solution prepared by dissolving 6 parts by weight of Exemplified Compound (14) and 10 parts by weight of a polycarbonate "Panlite L-1250" (Teijin Chemical Co., Ltd.) into 90 parts by weight of 1,2-dichloroethane, so that the thickness thereof after drying becomes 11 microns.

The thus prepared light-sensitive body was subjected to measurements similar to those in Example 1. The results are shown in Table 3.

TABLE 3

| | 1st | 100th |
|---|---|---|
| $V_A$ (V) | −960 | −965 |
| $E\frac{1}{2}$ (lux.sec) | 3.4 | 3.5 |
| $V_R$ (V) | 0 | 0 |

Further, this light-sensitive body was applied to an electrophotographic copier "U-Bix 2000 R" (manufactured by Konishiroku Photo• Industry Co., Ltd.) to carry out reproductions of an image, then copies of the image true to the original, highly contrasty, and excellent in the gradation were obtained. The light-sensitive body enabled making satisfactory 10,000 copies without changing the exposure; the image quality, even after the 10,000 copying operations, was on the same level as the initial ones. The surface potential, sensitivity (half-decay exposure) and residual potential were measured. The results are shown in Table 4.

TABLE 4

| | After making 10,000 copies |
|---|---|
| $V_A$ (V) | −975 |
| $E\frac{1}{2}$ (lux.sec) | 3.7 |
| $V_R$ (V) | −5 |

Control 2

A control light-sensitive body was prepared in the same manner as in Example 2 with the exception that as the carrier-transport material there was used a derivative of a carbazole having the formula:

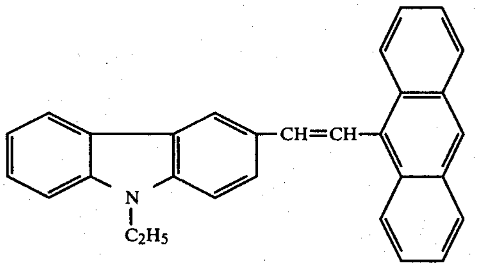

and the resulting light-sensitive body was subjected to measurements similar to those in Example 2. The results are as shown in Table 5.

TABLE 5

| | 1st copying | 100th copying | After making 10,000 copies |
|---|---|---|---|
| $V_A$ (V) | −815 | −890 | −945 |
| $E\frac{1}{2}$ (lux.sec) | 5.2 | 6.3 | 7.7 |
| $V_R$ (V) | −30 | −55 | −120 |

As apparent from the table, it is found that the control light-sensitive body is remarkably inferior in the stability in the repeated copying operations to the light-sensitive body of the present invention.

EXAMPLE 3

A conductive support having the same interlayer as was used in Example 2 was coated thereon, then was coated with a carrier-generation layer by applying thereon a solution so that the coated amount after drying is 0.2 g/m², said solution being prepared by dissolving 1 part by weight of a bisazo pigment having the formula:

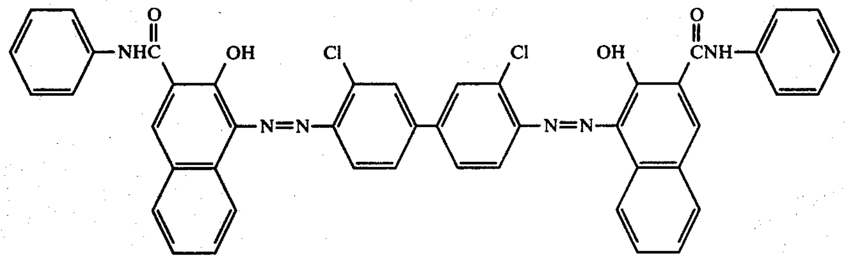

into 140 parts by weight of a mixture solution of ethylenediamine, n-butylamine, and tetrahydrofuran mixed in the ratio of 1.2:1.0:2.2, and was further coated with a carrier-transport layer by applying a solution prepared by dissolving 6 parts by weight of Exemplified Compound (10) and 10 parts by weight of methacrylic resin "Acrypet" (manufactured by Mitsubishi Rayon Co., Ltd.) into 90 parts by weight of 1,2-dichloroethane so that the thickness thereof after drying is 12 microns, thus preparing an electrophotographic light-sensitive body of the present invention. The thus obtained light-sensitive body was subjected to measurements similar to those in Example 1. The E½ was 2.9 lux.sec., while the $V_R$ was 0(V).

EXAMPLE 4

A conductive support having the same interlayer as was used in Example 2 was coated thereon, then was coated with a 0.5-micron-thick carrier-generation layer by the vacuum deposition of N,N'-dimethyl perylene-3,4,9,10-tetracarboxylic acid diimide "Paliogen Maroon 3920" (C.I. No. 71130, manufactured by BASF). On this was coated a carrier-transport layer by applying a solution prepared by dissolving 6 parts by weight of Exemplified Compound (3) and 10 parts by weight of a polyester "Vylon 200" (manufactured by Toyobo Co., Ltd.) into 90 parts by weight of 1,2-dichloroethane so that the thickness thereof after drying is 11 microns, thus producing an electrophotographic light-sensitive body of the present invention.

The resulting light-sensitive body was subjected to measurements similar to those in Example 1, then the results were E½ = 5.6 lux.sec. and $V_R = -10$ V.

EXAMPLE 5

An aluminum foil-laminated conductive polyester film support was coated with a 0.05-micron-thick interlayer of a polyester "Vylon 200" (manufactured by Toyobo Co., Ltd.), and on this was coated a light-sensitive layer by applying a solution prepared by dissolving 1 part by weight of 4-(p-dimethylaminophenyl)-2,6-diphenyl-thiapyrylium perchlorate into 130 parts by weight of dichloromethane, into which were further well dissolved by stirring 10 parts by weight of a polycarbonate "Jupilon S-1000" (manufactured by Mitsubishi Gas Chemicals Co., Inc.) and 6 parts by weight of Exemplified Compound (16) so that the thickness thereof after drying is 12 microns, whereby an electrophotographic light-sensitive body of the present invention was prepared.

The initial characteristics and the characteristics after making 10,000 copies are as shown in Table 6.

TABLE 6

| | 1st copying | After making 10,000 copies |
|---|---|---|
| $V_A$ (V) | −935 | −955 |
| E½ (lux.sec) | 1.7 | 1.9 |
| $V_R$ (V) | 0 | 0 |

EXAMPLE 6

An electrophotographic light-sensitive body of the present invention was prepared in the same manner as in Example 5 with the exception that as the carrier-transport material, Exemplified Compound (28) was used, and the resulting light-sensitive body was subjected to measurements similar to those in Example 1. The characteristics in the first and 100th measurements were as shown in Table 7.

TABLE 7

| | 1st | 100th |
|---|---|---|
| $V_A$ (V) | −890 | −905 |
| E½ (lux.sec) | 2.3 | 2.5 |
| $V_R$ (V) | 0 | −5 |

Control 3

A control light-sensitive body was prepared in the same manner as in Example 5 with the exception that as the carrier-transport material there was used a carbazole derivative having the formula:

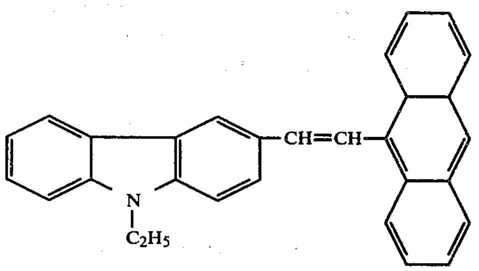

and the light-sensitive body was subjected to measurements similar to those in Example 6. The results are as shown in Table 8.

TABLE 8

| | 1st | 100th |
|---|---|---|
| $V_A$ (V) | −865 | −910 |
| E½ (lux.sec) | 3.6 | 4.9 |
| $V_R$ (V) | −25 | −45 |

The above table shows that the control light-sensitive body is remarkably inferior to the light-sensitive body of the present invention.

EXAMPLES 7 TO 10

Electrophotographic light-sensitive bodies of the present invention were prepared in the same manner as in Example 2 with the exception that Exemplified Compounds (4), (8), (15) and (17) were used, respectively, and these resulting light-sensitive bodies were subjected to the measurement similar to that in Example 1 to determine the sensitivities thereof (half-decay exposure), then the results were obtained as shown in Table 9.

TABLE 9

| | Exemplified compound | E½ (lux.sec) |
|---|---|---|
| Example 7 | (4) | 3.2 |
| Example 8 | (8) | 3.8 |
| Example 9 | (15) | 3.1 |
| Example 10 | (17) | 3.5 |

Control 4

A control light-sensitive body was prepared in the same manner as in Example 2 with the exception that as the carrier-transport material there was used a compound having the formula:

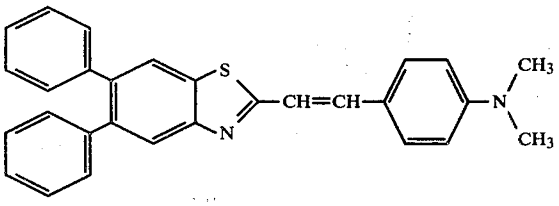

This light-sensitive body was subjected to similar measurements to those in Example 2. The results are shown in Table 10.

TABLE 10

| | 1st | 100th |
|---|---|---|
| $V_A$ (V) | −690 | −730 |
| $E_{\frac{1}{2}}$ (lux.sec) | 6.4 | 8.6 |
| $V_R$ (V) | −64 | −115 |

As apparent from the table, it is found that the control electrophotographic light-sensitive body shows very large deterioration in repetitive use as compared with the electrophotographic light-sensitive bodies of the present invention.

Control 5

A control light-sensitive body was prepared in the same manner as in Example 3 with the exception that as the carrier-transport material there was used a compound having the formula:

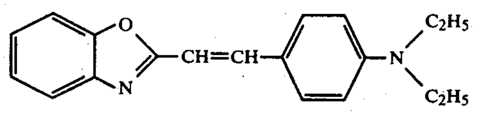

This light-sensitive body was subjected to the measurement similar to that of Example 3. The $E_{\frac{1}{2}}$ was 7.3 lux.sec. Thus the sensitivity of the control light-sensitive body was remarkably lower than that of the electrophotographic light-sensitive body of the present invention in Example 3.

Control 6

A control light-sensitive body was prepared in the same manner as in Example 4 with the exception that as the carrier-transport material there was used a compound having the formula:

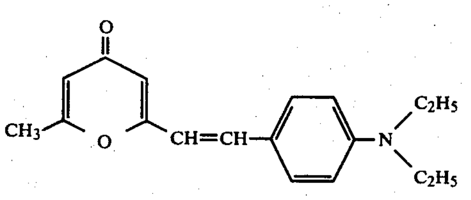

The prepared light-sensitive body was subjected to similar measurements to those in Example 4. The $E_{\frac{1}{2}}$ was 10.5 lux. sec., while the $V_R$ was −92 V. As apparent from the results, the control light-sensitive body was remarkably inferior to the light-sensitive body of the present invention in Example 4.

BRIEF DESCRIPTION OF THE DRAWINGS

FIG. 1 to FIG. 6 are the respective sectional views of examples of the mechanical composition of the electrophotographic light-sensitive body of the present invention, wherein

Figure 1:
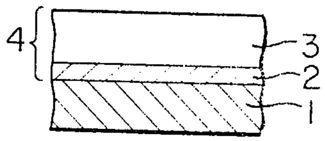
Figure 2:
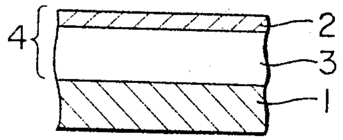
Figure 3:
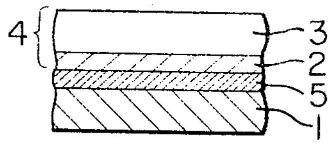
Figure 4:
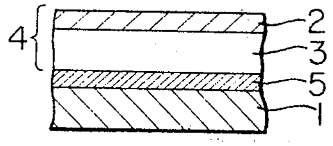
Figure 5:
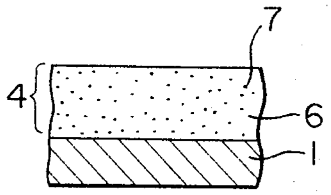
Figure 6:
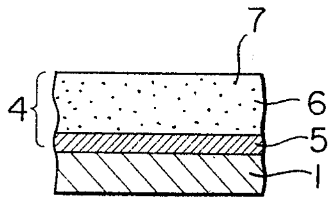

1 . . . conductive support,
2 . . . carrier-generation layer,
3 . . . carrier-transport layer,
4 . . . light-sensitive layer,
5 . . . interlayer,
6 . . . layer containing carrier-transport material, and
7 . . . carrier-generation material.

We claim:

1. An electrophotographic light-sensitive element comprising a conductive support which supports a light-sensitive layer containing a carbazole derivative of the formula:

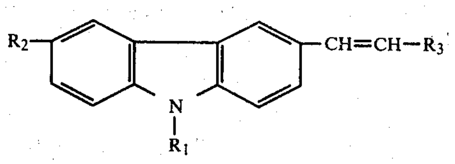

wherein $R_1$ is an aryl group, $R_2$ is hydrogen, a halogen, an alkyl, an alkoxy, an amino or hydroxy group, and $R_3$ is an aryl, or a heterocyclic group.

2. The electrophotographic light-sensitive element of claim 1, wherein said aryl group in $R_1$ is a phenyl group or a naphthyl group.

3. The electrophotographic light-sensitive element of claim 1, wherein said aryl group in $R_1$ is unsubstituted phenyl, unsubstituted naphthyl, phenyl or naphthyl substituted by an alkyl group having 1 to 4 carbon atoms, an alkoxy group having 1 to 4 carbon atoms, a dimethylamino group, a diethylamino group, chlorine or bromine.

4. The electrophotographic light-sensitive element of claim 1, wherein $R_2$ is selected from the group consisting of hydrogen, chlorine atom, bromine atom, an alkyl group having 1 to 4 carbon atoms, an alkoxy group having 1 to 4 carbon atoms, a dimethylamino group, a diethylamino group and hydroxy group.

5. The electrophotographic light-sensitive element of claim 1, wherein $R_3$ is selected from the group consisting of a phenyl group, a naphthyl group, an anthryl group, a furyl group, a thienyl group, a carbazyl group, a benzfuryl group and a benzthienyl group, which may be substituted by an alkyl group having 1 to 4 carbon atoms, an alkoxy group having 1 to 4 carbon atoms, a phenyl group, a dimethylamino group, a diethylamino group, a diphenylamino group, a hydroxy group or a halogen atom.

6. The electrophotographic light-sensitive element of claim 3, wherein $R_2$ is selected from the group consisting of hydrogen, chloride atom, bromine atom, an alkyl group having 1 to 4 carbon atoms, an alkoxy group having 1 to 4 carbon atoms, a dimethylamino group, a diethylamino group and hydroxy group; wherein $R_3$ is selected from the group consisting of a phenyl group, a naphthyl group, an anthryl group, a furyl group, a thienyl group, a carbazyl group, a benzfuryl group and a benzthienyl group, which may be substituted by an alkyl group having 1 to 4 carbon atoms, an alkoxy group having 1 to 4 carbon atoms, a phenyl group, a dimethylamino group, a diethylamino group, a diphenylamino group, a hydroxy group or a halogen atom.

7. The electrophotographic light-sensitive element of claim 1, wherein said light-sensitive layer further comprises a carrier-generation material.

8. The electrophotographic light-sensitive element of claim 6, wherein said light-sensitive layer further comprises a carrier-generation material.

9. The electrophotographic light-sensitive element of claim 7, wherein said light-sensitive layer comprises a layer containing said carrier-generation material and a layer containing said carbazole derivative.

10. The electrophotographic light-sensitive element of claim 8, wherein said light-sensitive layer comprises a layer containing said carrier-generation material and a layer containing said carbazole derivative.

11. The electrophotographic light-sensitive element of claim 1, further comprising an interlayer between said light-sensitive layer and said conductive support.

12. The electrophotographic light-sensitive element of claim 1, wherein said light-sensitive layer further comprises a spectral sensitizing dye selected from the group consisting of triphenyl methane dye, xanthene dye, thiazine dye, oxazine dye, cyanine dye, styryl dye, pyrylium salt dye and 3, 3′-dicarbazolyl methane dye.

13. The electrophotographic light-sensitive element of claim 1, wherein said light-sensitive layer further comprises a binder.

14. The electrophotographic light-sensitive element of claim 9, wherein said layer containing said carrier-generation material has a thickness of 0.05 to 3 microns and said layer containing said carbazole derivative has a thickness of from 5 to 30 microns.

* * * * *